United States Patent
Suzuki et al.

(10) Patent No.: US 7,612,066 B2
(45) Date of Patent: Nov. 3, 2009

(54) COMPOSITION CONTAINING BENZAMIDINE DERIVATIVE AND METHOD FOR STABILIZING BENZAMIDINE DERIVATIVE

(75) Inventors: Yasuyuki Suzuki, Kakamigahara (JP); Satoshi Fujioka, Kakamigahara (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 107 days.

(21) Appl. No.: 10/590,976

(22) PCT Filed: Mar. 4, 2005

(86) PCT No.: PCT/JP2005/003742

§ 371 (c)(1),
(2), (4) Date: Aug. 28, 2006

(87) PCT Pub. No.: WO2005/084679

PCT Pub. Date: Sep. 15, 2005

(65) Prior Publication Data

US 2007/0208016 A1   Sep. 6, 2007

(30) Foreign Application Priority Data

Mar. 4, 2004   (JP) ............... 2004-061472

(51) Int. Cl.
*A61K 31/5377* (2006.01)
*A61K 31/496* (2006.01)
*A61K 31/454* (2006.01)
*A61K 31/4035* (2006.01)

(52) U.S. Cl. ............... 514/232.8; 514/254.08; 514/323; 514/414

(58) Field of Classification Search ......... 514/414, 514/416, 231.5, 254.09, 323, 422, 232.8, 514/254.08; 544/111; 548/471, 465, 518; 546/201

See application file for complete search history.

(56) References Cited

U.S. PATENT DOCUMENTS

| 7,244,730 B2 * | 7/2007 | Suzuki et al. ............ 514/235.2 |
| 2004/0157769 A1 | 8/2004 | Sawai et al. |
| 2005/0004204 A1 | 1/2005 | Suzuki et al. |

FOREIGN PATENT DOCUMENTS

| EP | 1 457 207 A1 | 9/2004 |
| JP | 10-67659 A | 3/1998 |
| JP | 2002-363097 A | 12/2002 |
| WO | WO-02/085855 A1 | 10/2002 |

OTHER PUBLICATIONS

FDA drug Application No. NDA #019437 (Aminosyn II).*

* cited by examiner

*Primary Examiner*—Yong Chu
(74) *Attorney, Agent, or Firm*—Birch, Stewart, Kolasch & Birch, LLP

(57) ABSTRACT

The present invention provides a composition containing a benzamidine derivative that does not decompose even when placed under humidification conditions and a method for stabilizing a benzamidine derivative. According to the present invention, decomposition reaction of a benzamidine derivative can be suppressed by adding to a benzamidine derivative represented by general formula (I) or a pharmacologically acceptable salt thereof, at least one type of electrolyte selected from the group consisting of halide salts of alkaline metal or alkaline earth metal and alkaline metal salts or alkaline earth metal salts of perchloric acid.

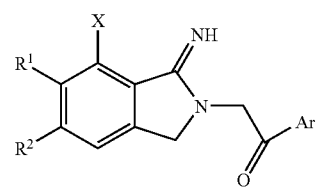

(I)

Figure 1:
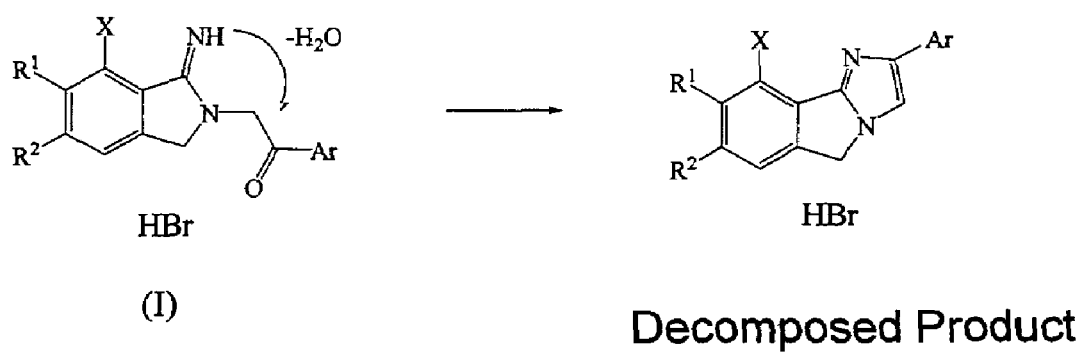

8 Claims, 1 Drawing Sheet (I)                    Decomposed Product

COMPOSITION CONTAINING BENZAMIDINE DERIVATIVE AND METHOD FOR STABILIZING BENZAMIDINE DERIVATIVE

This application is a national phase application of International Application No. PCT/JP2005/003742 filed on Mar. 4, 2005, which claims priority on Japanese Application No. 2004-061472 filed on Mar. 4, 2004.

TECHNICAL FIELD

The present invention relates to a composition containing a benzamidine derivative and a method for stabilizing a benzamidine derivative.

BACKGROUND ART

The benzamidine derivative represented by the following general formula (I) is a compound that has an antagonistic action on a thrombin receptor and is expected to provide an excellent effect in the treatment and prophylaxis of diseases with which thrombin is associated, such as, thrombosis, vascular restenosis, cerebral infarction, cardiac disease, disseminated intravascular coagulation syndrome, hypertension, inflammatory disease, rheumatism, asthma, glomerular nephritis, osteoporosis, nervous disease, malignant tumor and the like (for example, see Patent Reference 1).

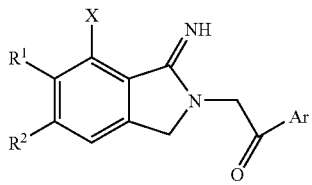

(I)

Patent Reference 1: International Publication WO 02/085855

DISCLOSURE OF INVENTION

Problem to be Solved by the Invention

Although the benzamidine derivative represented by the general formula (I) or a pharmacologically acceptable salt thereof is a highly stable compound on its own, due to the coexistence with a formulation additive under humidification/heating conditions in a solid state, and due to a high pH state in a liquid state, a decomposition product is sometimes generated by a reaction as shown in FIG. 1. A method has been devised, which enforces moisture proof packaging, as a method to increase the stability of the benzamidine derivative or the pharmacologically acceptable salt thereof; however, in this case, there is a problem of leading to an increase in the manufacturing costs.

Means for Solving the Problem

In view of the above, the present inventors, as a result of earnest study into solving the problems, reached completion of the present invention with the surprising observation that by adding to a benzamidine derivative represented by chemical formula (I), at least one type of electrolyte selected from the group consisting of halide salts of alkaline metal or alkaline earth metal and alkaline metal salts or alkaline earth metal salts of perchloric acid, the benzamidine derivative could be stabilized. An object of the present invention is to provide a composition containing a benzamidine derivative wherein decomposition does not occur readily even when placed under humidification/heating conditions and a method for stabilizing a benzamidine derivative. That is to say, a composition according to the present invention relates to:

(1) a composition comprising:
  a benzamidine derivative represented by the following formula (I) or a pharmacologically acceptable salt thereof; and
  at least one type of electrolyte selected from the group consisting of halide salts of alkaline metal or alkaline earth metal and alkaline metal salts or alkaline earth metal salts of perchloric acid:

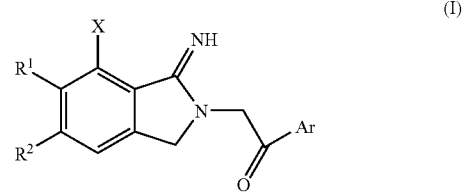

(I)

[wherein $R^1$ and $R^2$ are the same as or different from each other and each represents a hydrogen atom, a methoxy group or an ethoxy group, X represents a hydrogen atom or a halogen atom, and Ar represents a phenyl group that may be substituted with one or not less than two substituents selected from the group consisting of a methyl group, an ethyl group, a methoxy group, an ethoxy group, a t-butyl group, a morpholinyl group, or a substituent represented by the following formula (XX),

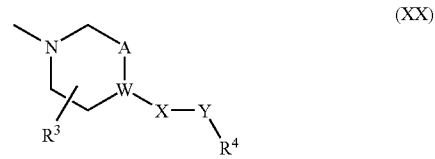

(XX)

wherein W represents CH or a nitrogen atom, A represents $CH_2$ or a single bond, $R^3$ represents a hydrogen atom or $OR^5$, X represents $CH_2$, an oxygen atom, a single bond or a carbonyl group, Y represents a single bond or a $C_{1-4}$ alkyl group, $R^4$ represents a hydrogen atom, $OR^6$, a cyano group or $COOR^7$, and $R^5$, $R^6$ and $R^7$ represent a hydrogen atom or a $C_{1-4}$ alkyl group.], (2) the composition according to item (1), wherein the $R^1$ and $R^2$ represent an ethoxy group, and the X represents a fluorine atom, (3) a composition comprising:
  a benzamidine derivative represented by any one of the chemical formulae (II) to (VIII) or a pharmacologically acceptable salt thereof; and
  at least one type of electrolyte selected from the group consisting of halide salts of alkaline metal or alkaline earth metal and alkaline metal salts or alkaline earth metal salts of perchloric acid:

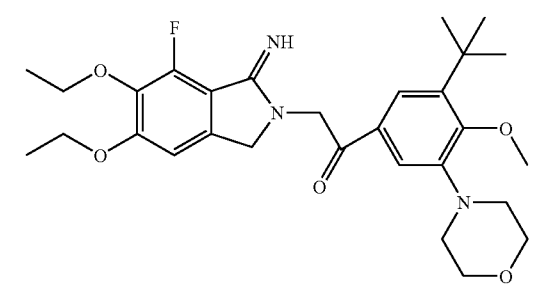
(II)

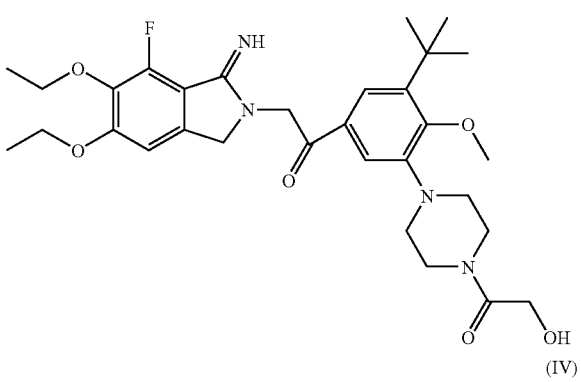
(III)

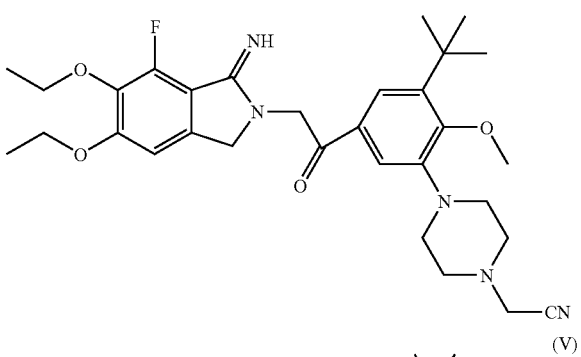
(IV)

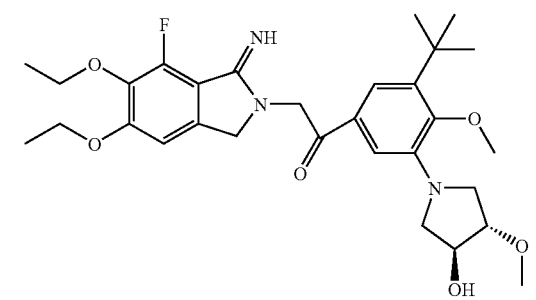
(V)

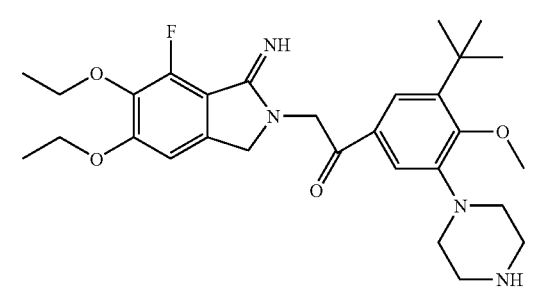
(VI)

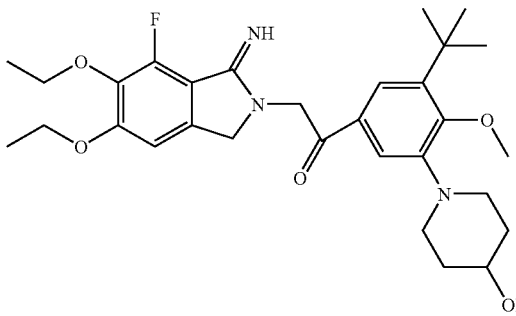
(VII)

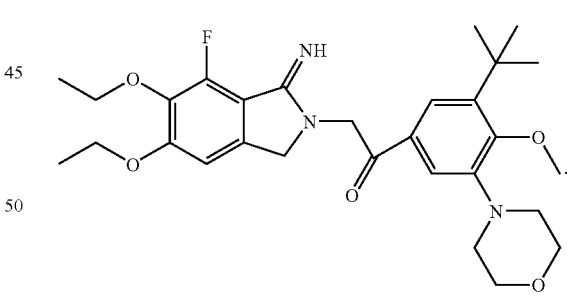
(VIII)

(4) the composition according to any one of items (1) to (3), wherein an amount of the electrolyte based on one part by weight of the benzamidine derivative or the pharmacologically acceptable salt thereof is from 0.5 parts by weight to 30 parts by weight, (5) the composition according to item (3), wherein the benzamidine derivative or the pharmacologically acceptable salt thereof is a hydrobromic acid salt of the benzamidine derivative represented by the following chemical formula (II):

(II)

In addition, a method for stabilizing a benzamidine derivative of the present invention relates to:

(6) a method for stabilizing a benzamidine derivative, comprising the step of:
adding to a benzamidine derivative represented by the chemical formula (I) or a pharmacologically acceptable salt thereof, at least one type of electrolyte selected from the group consisting of halide salts of alkaline metal or alkaline earth metal and alkaline metal salts or alkaline earth metal salts of perchloric acid, (7) a method for stabilizing a benzamidine derivative, comprising the step of:

adding to a benzamidine derivative represented by the chemical formula (II) or a pharmacologically acceptable salt thereof, at least one type of electrolyte selected from the group consisting of halide salts of alkali metal or alkaline earth metal and alkali metal salts or alkaline earth metal salts of perchloric acid:

(8) the method according to item (6) or (7), wherein an amount of the electrolyte based on one part by weight of the benzamidine derivative is from 0.5 parts by weight to 30 parts by weight, and the like.

Advantageous Effect of Invention

The composition containing benzamidine derivative and the method for stabilizing the composition containing the benzamidine derivative according to the present invention has the following advantageous effects. That is to say, the composition of the benzamidine derivative with excellent stability can be formulated in order to prevent decomposition reaction from occurring under humidification conditions; in addition, as moisture proof packaging is not needed, the manufacturing costs can be lowered.

BRIEF DESCRIPTION OF DRAWING(S)

FIG. 1 illustrates decomposition of a benzamidine derivative.

BEST MODE FOR CARRYING OUT THE INVENTION

The embodiment is an example to describe the present invention, and is not intended to limit the present invention solely to this embodiment. The present invention can be carried out in various forms, as long as they do not depart from the spirit thereof.

The composition according to the present invention comprises (1) a benzamidine derivative or a pharmacologically acceptable salt thereof and (2) at least one type of electrolyte selected from the group consisting of halide salts of alkaline metal or alkaline earth metal and alkaline metal salts or alkaline earth metal salts of perchloric acid.

The benzamidine derivative used in the present invention can be synthesized by the method described in, for example, International Publication WO 02/085855, and the examples of the benzamidine derivate include benzamidine compound represented by chemical formula (I).

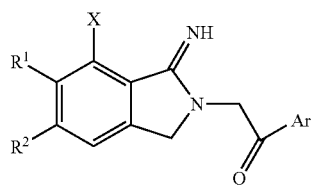

(I)

[wherein $R^1$ and $R^2$ are the same as or different from each other, and each represents a hydrogen atom, a methoxy group or an ethoxy group, X represents a hydrogen atom or a halogen atom, and Ar represents a phenyl group that may be substituted with one or not less than two substituents selected from the group consisting of a methyl group, an ethyl group, a methoxy group, an ethoxy group, a t-butyl group, a morpholinyl group, or a substituent represented by the following formula (XX),

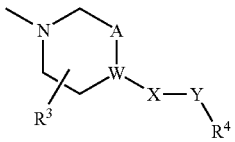

(XX)

wherein W represents CH or a nitrogen atom, A represents $CH_2$ or a single bond, $R^3$ represents a hydrogen atom or $OR^5$, X represents $CH_2$, an oxygen atom, a single bond or a carbonyl group, Y represents a single bond or a $C_{1-4}$ alkyl group, $R^4$ represents a hydrogen atom, $OR^6$, a cyano group or $COOR^7$, $R^5$, $R^6$ and $R^7$ represent a hydrogen atom or a $C_{1-4}$ alkyl group.].

The term "halogen atom" used in the present invention means a fluorine atom, a chlorine atom, a bromine atom, an iodide atom and the like, preferably the fluorine atom or the chlorine atom, and more preferably the fluorine atom. The term "$C_{1-4}$ alkyl group" used in the present invention means a linear or branched alkyl group having 1 to 4 carbons, and examples of "$C_{1-4}$ alkyl group" include a methyl group, an ethyl group, a n-propyl group, an iso-propyl group, a n-butyl group, a iso-butyl group, a sec-butyl group, a tert-butyl group and the like.

The use of compounds A to G shown in Table 1 may be preferred as the benzamidine compound represented in chemical formula (I) used the present invention, and their respective names are as follows:

A: 1-(3-tert-butyl-4-methoxy-5-morpholinophenyl)-2-(5,6-diethoxy-7-fluoro-1-imino-1,3-dihydroisoindol-2-yl)ethanone, B: 1-{3-tert-butyl-5-[4-(2-hydroxyacetyl)piperazin-1-yl]4-methoxyphenyl}-2-(5,6-diethoxy-7-fluoro-1-imino-1,3-dihydroisoindol-2-yl)ethanone, C: (4-{3-tert-butyl-5-[2-(5,6-diethoxy-7-fluoro-1-imino-1,3-dihydroisoindol-2-yl)acetyl]-2-methoxyphenyl}piperazin-1-yl)acetonitrile, D: 1-{3-tert-butyl-5-[(3S,4S)-3-hydroxy-4-methoxypyrrolidin-1-yl]-4-methoxyphenyl}-2-(5,6-diethoxy-7-fluoro-1-imino-1,3-dihydroisoindol-2-yl)ethanone, E: 1-(3-tert-butyl-4-methoxy-5-piperazin-1-ylphenyl)-2-(5,6-diethoxy-7-fluoro-1-imino-1,3-dihydroisoindol-2-yl)ethanone, F: 1-[3-tert-butyl-5-(4-hydroxypiperidin-1-yl)-4-methoxyphenyl]-2-(5,6-diethoxy-7-fluoro-1-imino-1,3-dihydroisoindol-2-yl)ethanone, G: ethyl (4-{3-tert-butyl-5-[2-(5,6-diethoxy-7-fluoro-1-imino-1,3-dihydroisoindol-2-yl)-acetyl]-2-methoxyphenyl}piperazin-1-yl)acetate.

Among these, the use of 1-(3-tert-butyl-4-methoxy-5-morpholinophenyl)-2-(5,6-diethoxy-7-fluoro-1-imino-1,3-dihydroisoindol-2-yl)ethanone (compound A in Table 1) is particularly preferred, in which case, the use of the hydrobromic acid salt thereof is preferred.

TABLE 1

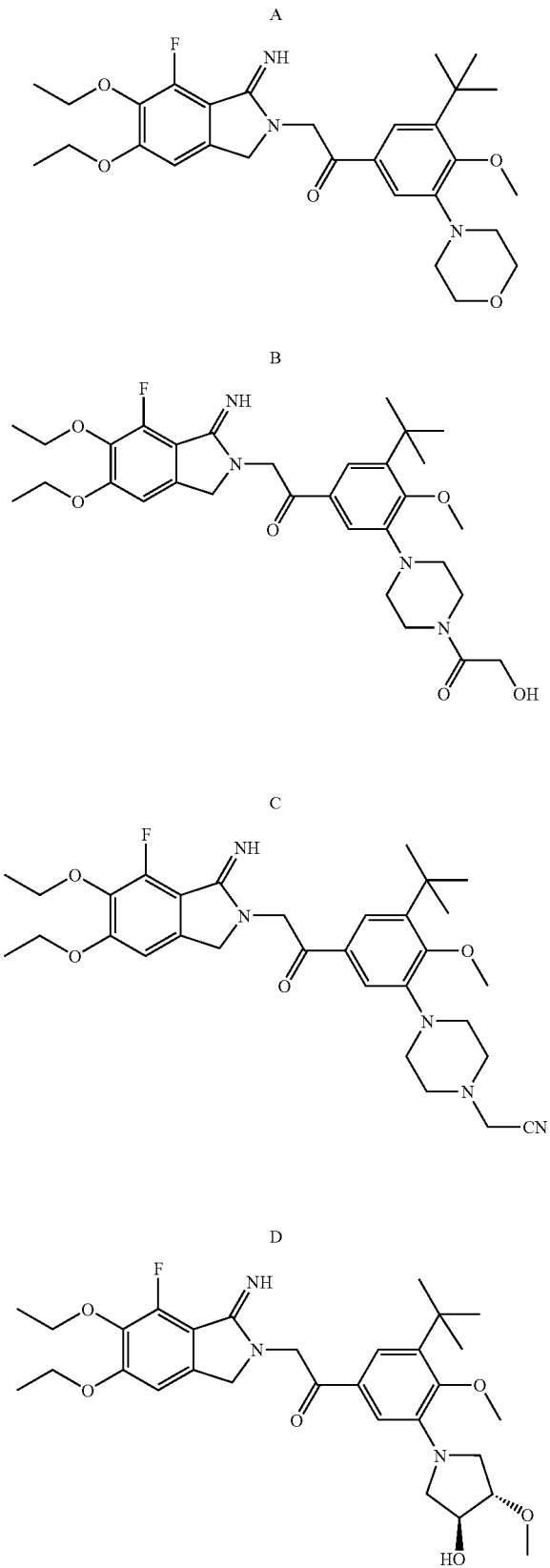

TABLE 1-continued

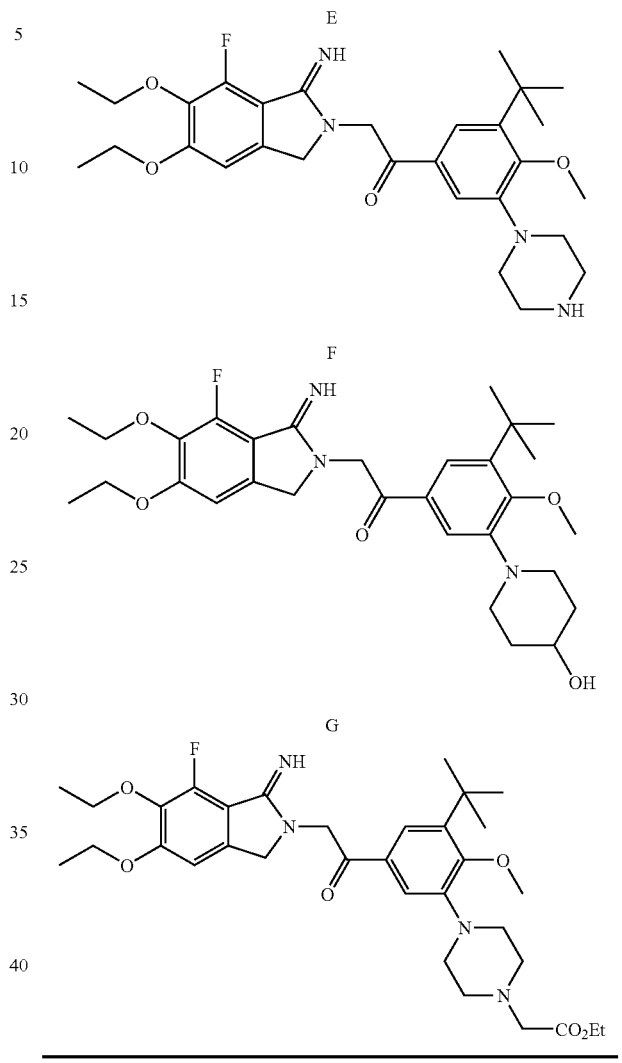

The benzamidine derivative used in the present invention may be a free form or a pharmacologically acceptable salt thereof. Herein, there is no limitation to a "pharmacologically acceptable salt" used in the present invention, as long as it forms a salt with the compound according to the present invention and is pharmacologically acceptable; preferred examples include hydrohalic acid salts (for example, hydrochloric acid salt, hydrobromic acid salt, hydroiodic acid salt and the like), inorganic acid salts (for example, sulfate, nitrate, perchlorate, phosphate, carbonate, bicarbonate and the like), organic carboxylates (for example, acetate, maleate, tartrate, fumarate, citrate and the like), organic sulfonates (for example, methanesulfonate, ethanesulfonate, benzenesulfonate, toluenesulfonate, camphor sulfonate and the like), amino acids (for example, aspartate, glutamate and the like), quaternary ammonium salts, alkaline metal salts (for example, sodium salt, potassium salt and the like), alkaline earth metal salts (for example, magnesium salt, calcium salt and the like), and the like; among which, the use of hydrobromic acid salt is the most preferable.

Any salt containing a halide ion or a perchlorate ion may be used as the electrolyte used in the present invention, for example, the use of a halide salt of an alkaline metal or an alkaline earth metal or an alkaline metal salt or an alkaline earth metal salt of perchloric acid is preferred. More specifically, the use of NaCl, KCl, $MgCl_2$, $CaCl_2$, KBr, or KI is preferred.

There is no particular limitation on an amount of electrolyte used in the present invention, which can be adjusted according to the type and amount of benzamidine derivative, the dosage form of the preparation, the type of the electrolyte, and the like. Based on one part by weight of the benzamidine derivative, the amount of electrolyte is generally from 0.5 to 30 parts by weight, preferably from 1 to 20 parts by weight and more preferably from 1.5 to 7.5 parts by weight.

There is no particular limitation in the dosage form when formulating the composition containing the benzamidine derivative according to the present invention, which can be made in any dosage form, for example, tablets, granules, powders, fine granules and the like. Additive generally used in a formulation step, such as diluents, binders, coating agents, colorants, flavorants and the like may also be included during formulation.

There is no particular limitation on the one-time dose of the benzamidine derivative used in the present invention, which can be adjusted according to the dosage form, disease, symptom, age, body weight, sex and the like. The one-time dose is generally from 0.1 mg to 500 mg, preferably from 0.5 mg to 200 mg, and more preferably from 1 mg to 100 mg.

The present invention also provides a method for stabilizing the benzamidine derivative comprising the step of adding to the benzamidine derivative represented by the chemical formula (I) or pharmacologically acceptable salt thereof, at least one type of electrolyte selected from the group consisting of halide salts of alkaline metal or alkaline earth metal and alkaline metal salts or alkaline earth metal salts of perchloric acid.

The present invention will be described in further detail with the following test examples and examples; however the scope of the present invention is not limited to these. Based on the description of the present invention, a variety of changes and modifications are possible by those skilled in the art, and these changes and modifications are also included in the present invention.

Tablet Stability Test

A preparation stability test of the composition containing a benzamidine derivative according to the present invention was carried out. The tablet stability test was carried out by analyzing with HPLC amounts of decomposition product (degradant) in tablets obtained in Example 1 and Example 2, which have been stored at 60° C. and 75% relative humidity (60° C./75% R.H.) for one week, and comparing with the reference group, which has been stored in cold. The test result of the tablet containing 1 mg of compound A is shown in Table 2, and the test result of the tablet containing 10 mg is shown in Table 3.

TABLE 2

| 1 mg T | Without NaCl | | With NaCl | |
|---|---|---|---|---|
| Storage for 1 W | Water content (%) | Degradant (%) | Water content (%) | Degradant (%) |
| Cold Storage | 0.43 | 0.16 | 0.84 | 0.13 |
| 60° C./75% R.H. | 1.27 | 11.34 | 5.19 | 2.85 |

TABLE 3

| 10 mg T | Without NaCl | | With NaCl | |
|---|---|---|---|---|
| storage for 1 W | Water content (%) | Degradant (%) | Water content (%) | Degradant (%) |
| Cold Storage | 0.10 | 0.09 | 0.77 | 0.08 |
| 60° C./75% R.H. | 0.89 | 1.30 | 6.46 | 0.73 |

As can be apparent from Tables 2 and 3, under heating/humidification conditions, in both the 1 mg tablet and the 10 mg tablet of the composition containing a benzamidine derivative according to the present invention, the increase in the amount of impurity was inhibited, as compared to the composition in which NaCl was not added.

Granule Stability Test

Next, the results of the granule stability test of the composition containing the benzamidine derivative according to the present invention are shown. In the present test, the amount of decomposition product after storing granules obtained in Examples 3 to 7 at 60° C. for 42 hours in 75% relative humidity was compared with that of the reference group. The results are shown in Table 4.

TABLE 4

| | 60° C./75% RH open for 42 hrs | |
|---|---|---|
| Ex | Sample | degradant (%) |
| — | Reference | 2.41 |
| 3 | NaCl | 1.49 |
| 4 | KCl | 1.74 |
| 5 | KBr | 1.09 |
| 6 | KI | 1.07 |
| 7 | $NaClO_4$ | 1.01 |

As can be apparent from Table 4, in all the granules of the composition containing the benzamidine derivative according to the present invention, the amount of decomposition product is less, as compared to the reference in which no electrolyte was added, and the stabilization effect due to the addition of the electrolyte was confirmed.

Lyophilized Powder Stability Test

The results of a lyophilized powder stability test of the composition containing a benzamidine derivative according to the present invention is shown in the following. In the present test, the amount of decomposition product after storing lyophilized powders obtained in Examples 8 to 23 for 60 hours at 60° C. and 75% relative humidity was compared with that of the reference group. The results are shown in Table 5.

TABLE 5

| Example | Compound | Electrolyte | Decomposition product (%) |
|---|---|---|---|
| Reference | B | — | 14.4 |
| 8 | | $NaClO_4$ | 6.0 |
| 9 | | KBr | 10.6 |
| Reference | C | — | 13.4 |
| 10 | | $NaClO_4$ | <7 |
| 11 | | KBr | <7 |

TABLE 5-continued

| Example | Compound | Electrolyte | Decomposition product (%) |
|---|---|---|---|
| Reference | D | — | 12.0 |
| 12 | | NaClO₄ | 5.8 |
| 13 | | KBr | 8.6 |
| Reference | F | — | 9.5 |
| 14 | | NaClO₄ | 4.6 |
| 15 | | KBr | 6.9 |
| Reference | E | — | 22.6 |
| 16 | | NaCl | 22.0 |
| 17 | | NaClO₄ | 8.3 |
| 18 | | KBr | 14.4 |
| 19 | | NaCl | 8.5 |
| 20 | | NaClO₄ | 5.8 |
| 21 | | KBr | 14.5 |
| Reference | G | — | 25.6 |
| 22 | | NaClO₄ | 10.5 |
| 23 | | KBr | 17.7 |

As can be apparent from Table 5, due to the addition of the electrolyte, the amount of decomposition product was less in all the benzamidine derivatives, as compared to the reference where no electrolyte was added, and the stabilization effect due to the addition of the electrolyte was confirmed.

EXAMPLE

In the following, as examples of compositions containing the benzamidine derivative according to the present invention, specific examples using compounds listed in Table 1 will be shown; however, the scope of the patent is not limited to these.

Example 1

According to the following procedure, a tablet containing compound A was prepared.
(1) Into a 1 L mixer were added 1 g of compound A, 117 g of lactose (manufactured by DMV Japan), 7.5 g of low-substituted hydroxypropyl cellulose (sometimes abbreviated simply as "L-HPC"; manufactured by Shin-Etsu Chemical) and 4.5 g of hydroxypropylmethyl cellulose (sometimes abbreviated simply as "HPMC"; manufactured by Shin-Etsu Chemical), which were mixed by stirring.
(2) Then, while stirring, a suitable amount of purified water in which 4.5 g of NaCl (Manufactured by Wako Pure Chemical) was dissolved was added for granulation.
(3) The granulated granule was dried at 60° C. for 5 hours in a dryer.
(4) To this were added 15 g of crystalline cellulose (manufactured by Asahi Kasei Chemicals) and 0.75 g of magnesium stearate (Manufactured by Mallinckrodt), which were then mixed in a vinyl bag.
(5) The powder was tableted with a single punch tabletting machine, so as to obtain a tablet containing 1 mg of compound A in one tablet (150 mg) with a tablet diameter of 6.5 mm.

Example 2

Changing the amount of compound A added, a tablet containing 10 mg of compound A in one tablet (150 mg) was obtained by an approximately identical procedure to Example 1.

Example 3

(1) Into a mixer (tablet grinder) were added 0.25 g of compound A, 27 g of lactose (Manufactured by DMV Japan), 1.5 g of low-substituted hydroxypropyl cellulose (manufactured by Shin-Etsu Chemical) and 0.9 g of HPMC (manufactured by Shin-Etsu Chemical), which were mixed by stirring.
(2) Weighing 940 mg of the powder prepared in (1) and 64 mg of NaCl (Manufactured by Wako Pure Chemical), a mortar was used for mixing, then, a suitable amount of purified water was added for granulation.
(3) The granulated granule was dried at 60° C. for 5 hours in a dryer, to obtain a granule containing compound A and NaCl.

Examples 4 to 7

Using each of KCl, KBr, KI and NaClO₄ instead of NaCl as an electrolyte, granules containing compound A were obtained in a similar procedure to Example 3.

Example 8

According to the following procedure, a lyophilized powder containing compound B was prepared.
(1) Over a microplate fitted with a filter were added dropwise 0.05 ml of a methanol water solution (volume ratio was MeOH:H₂O=3:7) containing 0.05 mg of compound B, 0.05 ml of water suspension containing 4 mg of Placebo component (component ratio: lactose/L-HPC/HPMC=92/5/3), and 0.025 ml aqueous solution containing 0.252 mg of NaClO₄.
(2) After stirring with a plate mixer, the plate was frozen in a freezer at −40° C. for 3 hours.
(3) Lyophilization was carried out for approximately 24 hours to obtain a lyophilized powder on the microplate.

Example 9

Using KBr instead of NaClO₄ as electrolyte, a lyophilized powder containing 0.05 mg of compound B, 4 mg of Placebo component, and 0.21 mg of KBr was obtained by a similar procedure to Example 8.

Examples 10 to 23

Lyophilized powders containing compounds C to G were prepared by a similar procedure to Example 8. The amounts of electrolyte added in the lyophilized powders obtained in Examples 8 to 23 are grouped in Table 6. In addition, for each compound, a lyophilized powder containing no electrolyte was prepared as a reference by preparing according to a similar procedure to Example 8.

TABLE 6

| Example | Compound | Electrolyte | Amount added (mg) |
|---|---|---|---|
| 8 | B | NaClO$_4$ | 0.252 |
| 9 |  | KBr | 0.210 |
| 10 | C | NaClO$_4$ | 0.252 |
| 11 |  | KBr | 0.210 |
| 12 | D | NaClO$_4$ | 0.252 |
| 13 |  | KBr | 0.210 |
| 14 | F | NaClO$_4$ | 0.252 |
| 15 |  | KBr | 0.210 |
| 16 | E | NaCl | 0.105 |
| 17 |  | NaClO$_4$ | 0.252 |
| 18 |  | KBr | 0.210 |
| 19 |  | NaCl | 0.210 |
| 20 |  | NaClO$_4$ | 0.504 |
| 21 |  | KBr | 0.420 |
| 22 | G | NaClO$_4$ | 0.252 |
| 23 |  | KBr | 0.210 |

INDUSTRIAL APPLICABILITY

The composition containing the benzamidine derivative and the method for stabilizing the composition containing the benzamidine derivative according to the present invention have the following effects: A preparation of the benzamidine derivative with excellent stability can be realized in order to prevent decomposition reaction from occurring under humidification conditions; in addition, as moisture proof packaging is not needed, thereby the manufacturing costs can be lowered.

What is claimed is:

1. A solid composition comprising:
   a benzamidine derivative represented by the following formula (I) or a pharmacologically acceptable salt thereof; and
   at least one type of electrolyte selected from the group consisting of halide salts of alkaline metal or alkaline earth metal and alkaline metal salts or alkaline earth metal salts of perchloric acid:

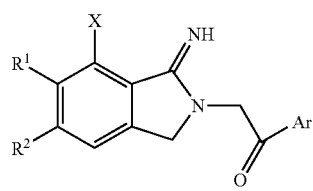

(I)

wherein R$^1$ and R$^2$ are the same as or different from each other and each represents a hydrogen atom, a methoxy group or an ethoxy group, X represents a hydrogen atom or a halogen atom, and Ar represents a phenyl group that may be substituted with one or not less than two substituents selected from the group consisting of a methyl group, an ethyl group, a methoxy group, an ethoxy group, a t-butyl group, a morpholinyl group, or a substituent represented by the following formula (XX),

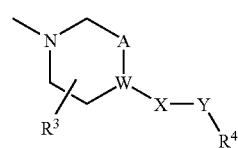

(XX)

wherein W represents CH or a nitrogen atom, A represents CH$_2$ or a single bond, R$^3$ represents a hydrogen atom or OR$^5$, X represents CH$_2$, an oxygen atom, a single bond or a carbonyl group, Y represents a single bond or a C$_{1-4}$ alkyl group, R$^4$ represents a hydrogen atom, OR$^6$, a cyano group or COOR$^7$, and R$^5$, R$^6$ and R$^7$ represent a hydrogen atom or a C$_{1-4}$ alkyl group.

2. The solid composition according to claim 1, wherein the R$^1$ and R$^2$ represent an ethoxy group, and the X represents a fluorine atom.

3. A solid composition comprising:
   a benzamidine derivative represented by any one of the chemical formulae (II) to (VIII) or a pharmacologically acceptable salt thereof; and
   at least one type of electrolyte selected from the group consisting of halide salts of alkaline metal or alkaline earth metal and alkaline metal salts or alkaline earth metal salts of perchloric acid:

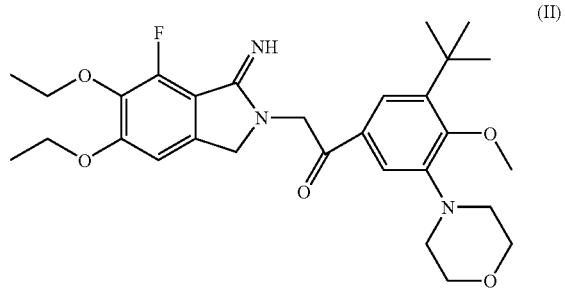

(II)

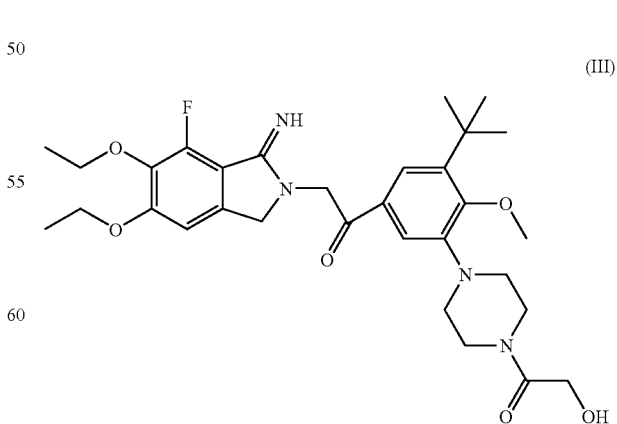

(III)

-continued

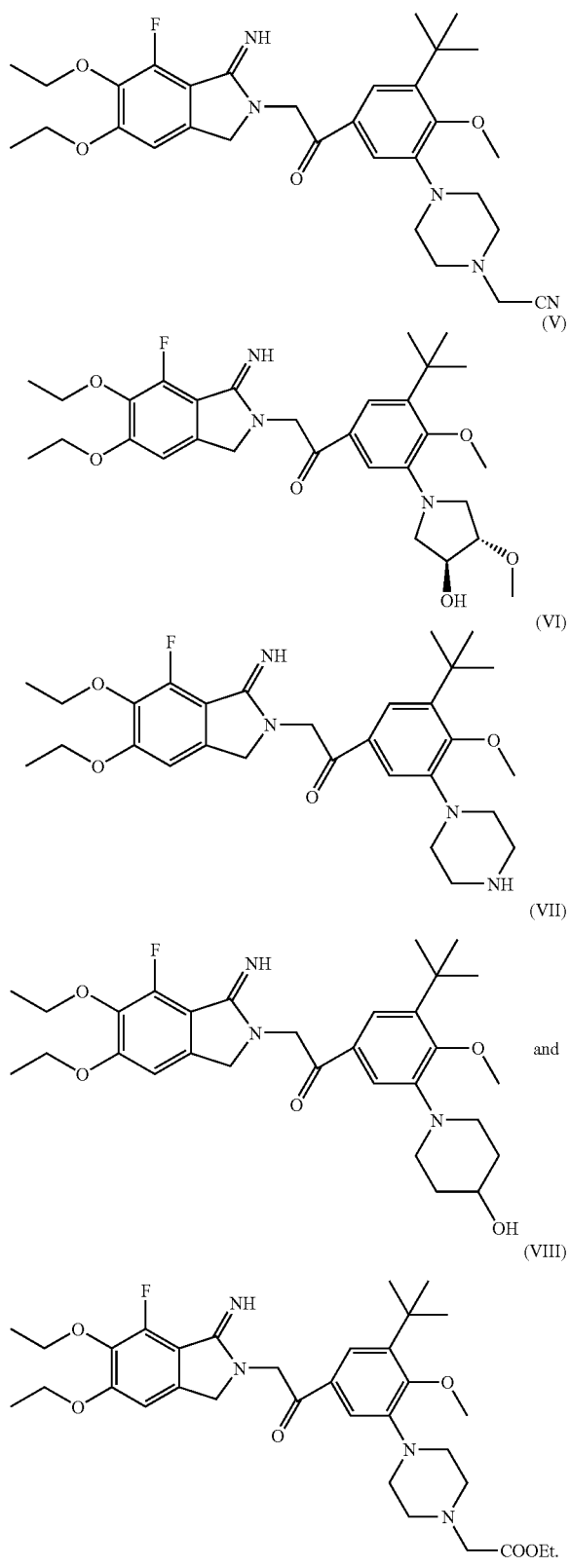

4. The solid composition according to any one of claims 1 to 3, wherein an amount of the electrolyte based on one part by weight of the benzamidine derivative or the pharmacologically acceptable salt thereof is from 0.5 parts by weight to 30 parts by weight.

5. The solid composition according to claim 3, wherein the benzamidine derivative or the pharmacologically acceptable salt thereof is a hydrobromic acid salt of the benzamidine derivative represented by the following chemical formula (II):

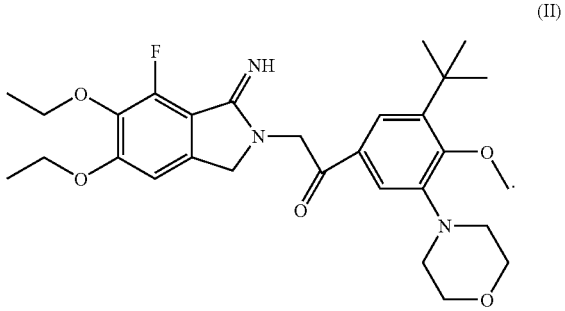

6. A method for stabilizing a benzamidine derivative, comprising the step of:
adding to a benzamidine derivative represented by the chemical formula (I) or a pharmacologically acceptable salt thereof, at least one type of electrolyte selected from the group consisting of halide salts of alkaline metal or alkaline earth metal and alkaline metal salts or alkaline earth metal salts of perchloric acid

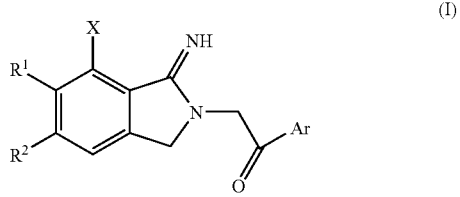

wherein $R^1$ and $R^2$ are the same as or different from each other and each represents a hydrogen atom, a methoxy group or an ethoxy group, X represents a hydrogen atom or a halogen atom, and Ar represents a phenyl group that may be substituted with one or not less than two substituents selected from the group consisting of a methyl group, an ethyl group, a methoxy group, an ethoxy group, a t-butyl group, a morpholinyl group, or a substituent represented by the following formula (XX),

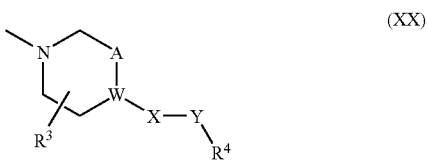

wherein, W represents CH or a nitrogen atom, A represents $CH_2$ or a single bond, $R^3$ represents a hydrogen atom or $OR^5$, X represents $CH_2$, an oxygen atom, a single bond or a carbonyl group, Y represents a single bond or a $C_{1-4}$ alkyl group, $R^4$ represents a hydrogen atom, $OR^6$, a cyano group or COOR⁷, R⁵, R⁶ and R⁷ represent hydrogen atoms or $C_{1-4}$ alkyl groups.

7. A method for stabilizing a benzamidine derivative, comprising the step of:

adding to a benzamidine derivative represented by any one of the chemical formula (II) to (VIII) or a pharmacologically acceptable salt thereof at least one type of electrolyte selected from the group consisting of halide salts of alkali metal or alkaline earth metal and alkali metal salts or alkaline earth metal salts of perchloric acid:

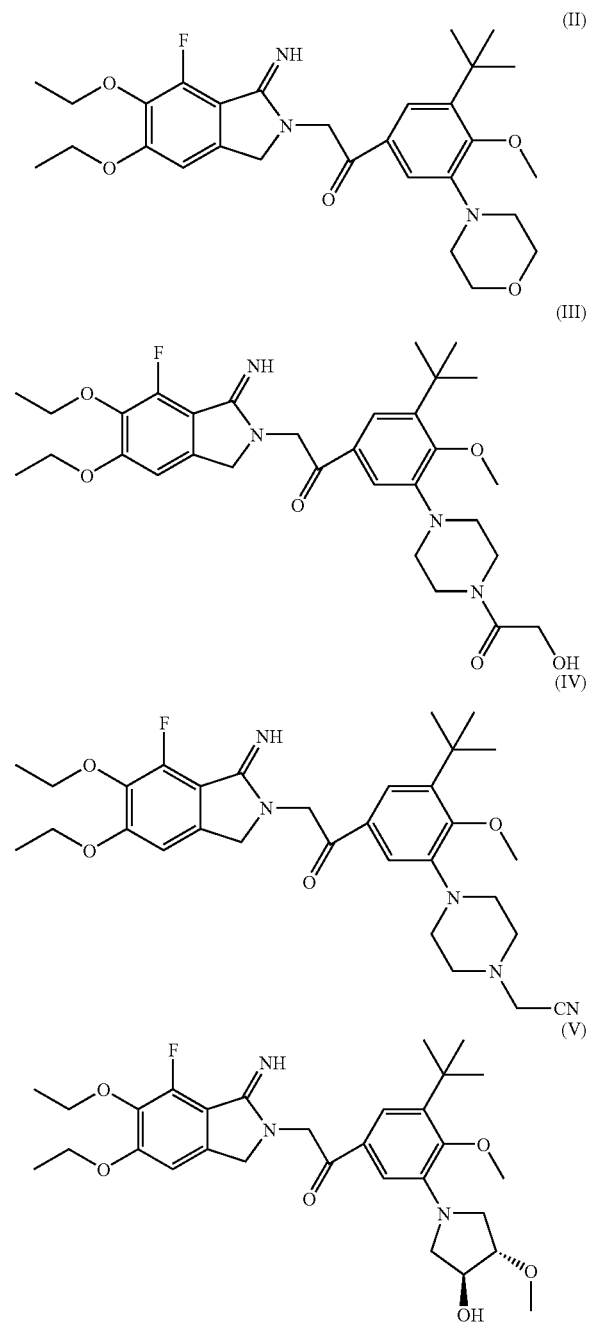

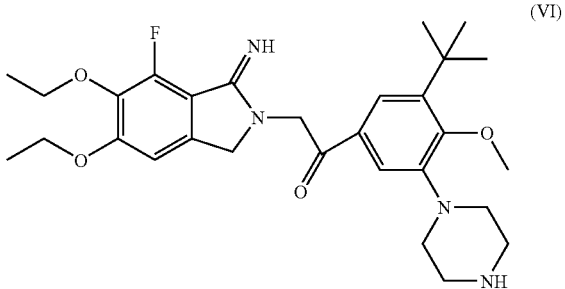

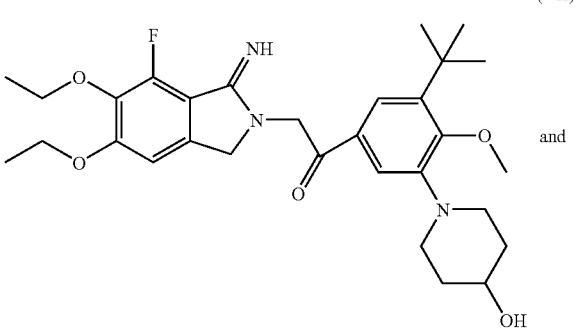

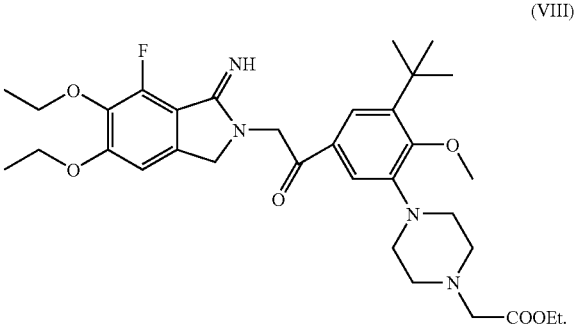

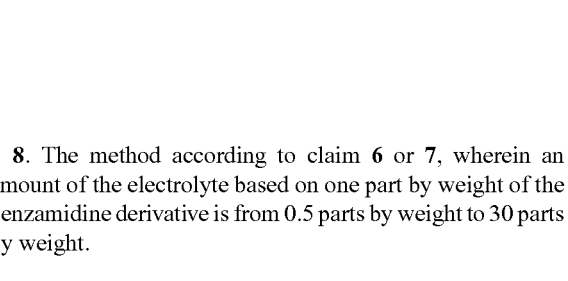

8. The method according to claim 6 or 7, wherein an amount of the electrolyte based on one part by weight of the benzamidine derivative is from 0.5 parts by weight to 30 parts by weight.

* * * * *